United States Patent [19]

Hoffman et al.

[11] Patent Number: 4,503,072

[45] Date of Patent: Mar. 5, 1985

[54] ANTIHYPERCHOLESTEROLEMIC COMPOUNDS

[75] Inventors: William F. Hoffman; Ta-Jyh Lee; Robert L. Smith, all of Lansdale, Pa.; Alvin K. Willard, Wilmington, Del.

[73] Assignee: Merck & Co., Inc., Rahway, N.J.

[21] Appl. No.: 621,393

[22] Filed: Jun. 18, 1984

Related U.S. Application Data

[62] Division of Ser. No. 452,176, Dec. 22, 1982.

[51] Int. Cl.³ .............. A61K 31/195; A61K 31/215; C07C 103/365; C07C 103/66; C07C 103/731; C07C 103/84

[52] U.S. Cl. .................... 424/305; 260/429.9; 260/448 R; 260/501.1; 260/501.15; 514/563; 514/63; 514/459; 514/538; 514/539; 544/358; 548/327; 549/292; 560/45; 560/49; 560/116; 560/119; 562/455; 562/498; 562/501

[58] Field of Search ........... 560/45, 116, 119; 562/455, 498, 501; 424/305, 309, 319

[56] References Cited

U.S. PATENT DOCUMENTS

| | | | |
|---|---|---|---|
| 3,983,140 | 8/1976 | Endo et al. | 549/292 |
| 4,231,938 | 11/1980 | Monaghan et al. | 549/292 |
| 4,282,155 | 8/1981 | Smith et al. | 424/279 X |
| 4,293,496 | 10/1981 | Willard | 562/501 X |
| 4,294,846 | 10/1981 | Albers-Schonberg et al. | 549/292 X |
| 4,343,814 | 8/1982 | Gullo et al. | 549/292 X |
| 4,351,844 | 9/1982 | Patchett et al. | 424/279 |

FOREIGN PATENT DOCUMENTS 0033538  8/1981  European Pat. Off. .

OTHER PUBLICATIONS

Chemical Abstracts, vol. 93, 1980, p. 608, abstract No. 94896s, Endo et al., "Tetrahydro ML-236B and its Derivatives".

*Primary Examiner*—Natalie Trousof
*Assistant Examiner*—Patricia M. Scott
*Attorney, Agent, or Firm*—Joseph F. DiPrima; Michael C. Sudol

[57] ABSTRACT

Compounds of general structural formula:

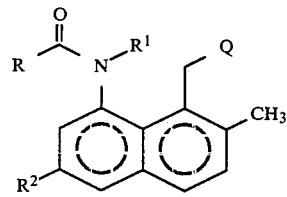

I wherein Q is:

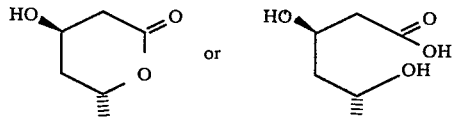

or pharmaceutically acceptable salts, $C_{1-3}$ alkyl esters or α-monoglyceride when Q is a dihydroxy acid are useful as antihypercholesterolemic agents for the treatment of atherosclerosis, familial hypercholesterolemia, hyperlipemia and like diseases. They also have useful antifungal activity.

9 Claims, No Drawings

ANTIHYPERCHOLESTEROLEMIC COMPOUNDS

This is a division of application Ser. No. 452,176, filed Dec. 22, 1982.

SUMMARY OF THE INVENTION

This invention is concerned with novel compounds of structural formula:

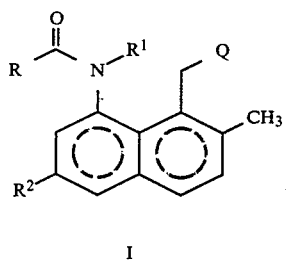

I wherein Q is:

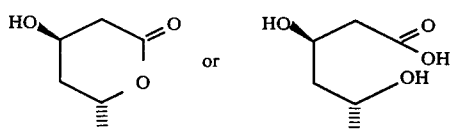

or pharmaceutically acceptable salts, $C_{1-3}$ alkyl esters or α-monoglycerides when Q is a dihydroxy acid.

It is also concerned with processes for preparing the novel compounds; antihypercholesterolemic pharmaceutical formulations comprising one of the novel compounds as active ingredient; a method of treating atherosclerosis, familial hypercholesterolemia, hyperlipemia and like diseases with a novel compound or pharmaceutical formulation thereof; antifungal formulations comprising one of the novel compounds as active ingredient; and a method of treating fungal infestations with a novel compound or formulation thereof.

BACKGROUND OF THE INVENTION

Compounds of structure II are known in the art also to have antihypercholesterolemic and antifungal activity.

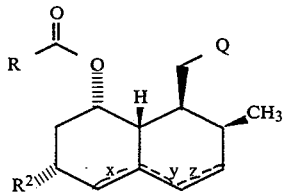

II

Many of the compounds of structure II where

is 2(S)-methylbutyryl are natural fermentation products: mevinolin ($R^2$=$CH_3$, X and Z are double bonds and Y is a single bond; Monaghan et al. U.S. Pat. No. 4,231,938); 4′a,5′-dihydromevinolin ($R^2$=$CH_3$, X and Y are single bonds and Z is a double bond; Albers-Schonberg et al., U.S. Pat. No. 4,294,846); compactin ($R^2$=H, X and Z are double bonds and Y is a single bond; Endo et al., U.S. Pat. No. 3,983,140); and 4′a,5′-dihydrocompactin ($R^2$=H, X and Y are single bonds and Z is a double bond; Gullo et al., U.S. Pat. No. 4,343,814).

Hydrogenation products of the above natural materials are also known to have antihypercholesterolemic and antifungal activity. The dihydro-analogs of mevinolin in which only X is a double bond or in which only Y is a double bond and tetrahydromevinolin are described by Patchett et al. in U.S. Pat. No. 4,351,844. Tetrahydro-compactin is described in Japanese Application (Kokai) No. 55009-024.

DETAILED DESCRIPTION OF THE INVENTION

The novel compound of this invention has structural formula:

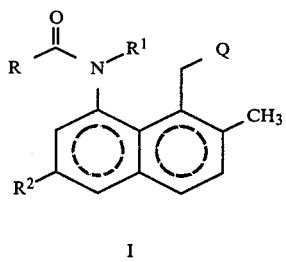

I wherein
Q is

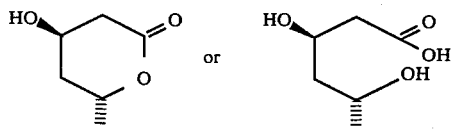

or a pharmaceutically acceptable salt, $C_{1-3}$ alkyl ester or α-monoglyceride when Q is a dihydroxy acid, wherein
$R^2$ is hydrogen or methyl;
R is
(1) $C_{1-10}$ alkyl, either straight or branched chain, such as methyl, ethyl, propyl, butyl, 1-methylpropyl, 1,1-dimethylpropyl, 1,1-diethylpropyl, 1-ethyl-1-methylpropyl, 1,1-dimethylethyl, 1,1-diethylbutyl or the like,
(2) $C_{3-6}$ cycloalkyl, such as cyclopropyl, cyclopentyl, or cyclohexyl,
(3) $C_{2-10}$ alkenyl, such as 1,1,2-trimethylprop-2-enyl, allyl or the like,
(4) halo-$C_{1-10}$ alkyl, wherein halo is chloro, bromo or fluoro, such as trifluoromethyl, 3,3,3-trifluoropropyl, 1,1-di(trifluoromethyl)propyl, or the like,
(5) phenyl,
(6) phenyl substituted by one or more of halo, $C_{1-3}$ alkyl, or $C_{1-3}$ alkoxy, wherein halo is fluoro, chloro or bromo, such as 3-methyl-4-fluorophenyl, 2,4-dichlorophenyl, 3,4-dimethoxyphenyl, or the like,
(7) phenyl-$C_{1-3}$ alkyl, such as benzyl, phenylethyl, or 2- or 3-phenylpropyl, or the like, or
(8) phenyl-$C_{1-3}$ alkyl wherein the phenyl group is substituted by one or more of halo, $C_{1-3}$ alkyl, or $C_{1-3}$ alkoxy, wherein halo is fluoro, chloro, or bromo, to form such as 3-methyl-4-fluorophenyl-, 2,4-dichlorophenyl-, 3,4-dimethoxyphenyl-$C_{1-3}$ alkyl, or the like; and $R^1$ is (1) hydrogen,
(2) $C_{1-3}$ alkyl, either straight or branched chain,
(3) $C_{3-6}$ cycloalkyl such as cyclopropyl, cyclopentyl or cyclohexyl,
(4) $C_{2-5}$ alkenyl such as vinyl, allyl or the like,
(5) halo-$C_{1-3}$ alkyl, such as 2,2,2-trifluoroethyl or the like, or
(6) benzyl, either unsubstituted or substituted by one or more of halo, $C_{1-3}$ alkyl, or $C_{1-3}$ alkoxy; and the dotted lines or circles represent all of the possible oxidation and reduction states of the bicyclic system such as naphthalene, dihydro-, tetrahydro-, hexahydro-, octahydro- and decahydronaphthalene.

It is preferred that R be 1-methylpropyl or 1,1-dimethylpropyl or 1-ethyl-1-methylpropyl. It is also preferred that $R^1$ be hydrogen or methyl.

With reference to the bicyclic moiety of the novel compounds it is preferred that the oxidation state be:

1',2',6',7',8',8'a-hexahydronaphthyl, (a);
1',2',3',4',6',7',8',8'a-octahydronaphthyl, (b);
1',2',3',5',6',7',8',8'a-octahydronaphthyl, (c);
1',2',4'a,5',6',7',8',8'a-octahydronaphthyl, (d); or
1',2',3',4',4'a,5',6',7',8',8'a-decahydronaphthyl, (e).

These partial structures (a) through (e) are shown below with the preferred stereochemical relationships of the substituents and ring fusions.

Partial Structures

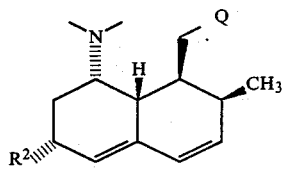
(a)

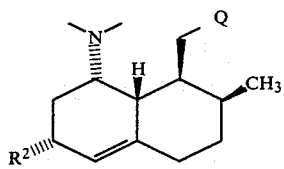
(b)

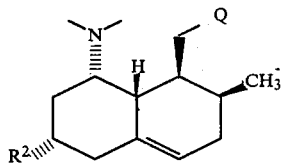
(c)

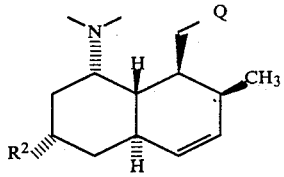
(d)

-continued
Partial Structures

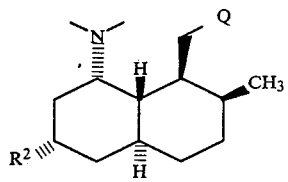
(e)

It is even more preferred that the partial structure be that shown as (a), (d), or (e).

Lactones $I_{a-e}$ can be hydolyzed with bases such as NaOH to yield the salts such as the sodium salt of dihydroxy acids $I_{a-e}$. The use of bases with other pharmaceutically acceptable cations affords salts of those cations. Careful acidification of the salts affords the hydroxy acids $I_{a-e}$ which revert to lactones $I_{a-e}$ at acidic pH. Treating Compound $I_{a-e}$ under acidic or basic catalysis with alcohols such as methanol, ethanol, propanol or the like, yields the corresponding esters of the dihydroxy acids, $I_{a-e}$ which also form a part of this invention.

The α-monoglyceride, or 2,3-dihydroxypropyl ester of dihydroxy acid $I_{a-e}$, is prepared by treating a salt of the dihydroxy acid in a solvent such as dimethyl formamide, hexamethylphosphoramide, N-methylpyrrolidone, or 1,3-dimethyl-2-imidazoline with 1-iodo-2,3-dihyroxypropane at 25°–150° C., preferably about 50° to 100° C. for about 3 to 10 hours, preferably about 4 to 8 hours.

The pharmaceutically acceptable salts of this invention include those formed from cations such as sodium, potassium, aluminum, calcium, lithium, magnesium, zinc and tetramethylammonium as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-(p-chlorobenzyl)-2-pyrrolidine-1'-yl-methylbenzimidazole, diethylamine, piperazine, and tris(hydroxymethyl)aminomethane.

The novel process for preparing the novel compounds of this invention is depicted by the following:

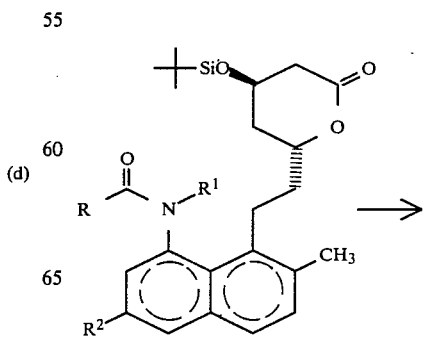

-continued

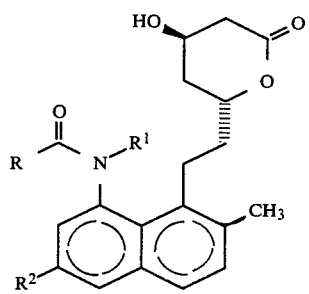

The process comprises deprotection of the 4-hydroxyl group by treatment of the dimethyl-tert-butylsilyl ether with a mixture of tetrabutylammonium fluoride and acetic acid in an ethereal solvent such as tetrahydrofuran, diethyl ether, 1,2-dimethoxyethane or the like. A ratio of 3 equivalents of tetrabutylammonium fluoride and 4 equivalents of acetic acid per equivalent of silyl ether is preferred. The reaction proceeds at about 10°–35° C., time periods of 1 to 4 days being required.

If desired, the dihydroxy acid I is formed by treatment of the lactone with at least an equivalent of base and back-titration with the same equivalent amount of an acid. At neutral or acid pH, the dihydroxy acid reverts to the lactone.

The compounds of this invention, especially the preferred polyhydronaphthyl embodiments thereof, are useful as antihypercholesterolemic agents for the treatment of atherosclerosis, familial hypercholesterolemia, hyperlipemia and like diseases. They may be administered orally or parenterally in the form of a capsule, a tablet, an injectable preparation or the like. It is usually desirable to use the oral route. Doses may be varied, depending on the age, severity, body weight and other conditions of patients but the daily dosage for adult humans is within a range of from about 2 mg to 2000 mg (preferably 10 to 100 mg) given in three or four divided doses. Higher doses may be favorably applied as required.

The compounds of this invention also have useful anti-fungal activities. For example, they may be used to control strains of *Penicillium sp., Aspergillus niger, Cladosporium sp., Cochiliobolus miyabeanus* and *Helminthosporium cynodnotis*. For those utilities they are admixed with suitable formulating agents, powders, emulsifying agents or solvents such as aqueous ethanol and sprayed or dusted on the plants to be protected.

EXAMPLE 1

6(R)-{2-[8'(S)-(2",2"-dimethylbutyrylamino)-2'(S),6'(S)-dimethyl-1',2',3',4',4'a(S),5',6',7',8',8'a(S)-decahydronaphthyl-1'(S)]ethyl}-4-(R)-hydroxy-3,4,5,6-tetrahydro-2H-pyran-2-one, (6)

Step A: Preparation of 6(R)-{2-[8'-oxo-2'(S),6'(S)-dimethyl-1',2',3',4',4'a(S),5',6',7',8',8'a(S)-decahydronaphthyl-1'(S)]ethyl}-4(R)-(dimethyl-tert-butylsilyloxy)-3,4,5,6-tetrahydro-2H-pyran-2-one, (2)

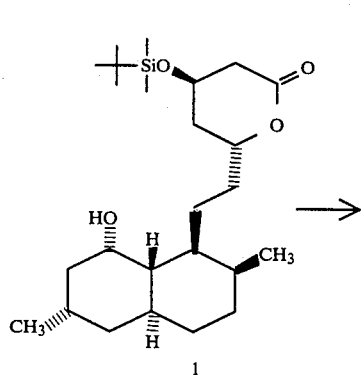

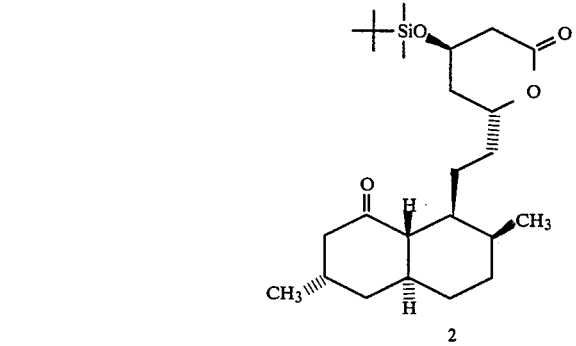

A solution of 25 ml of methylene chloride and 0.85 ml (0.0085 mole) of oxalyl chloride, under a dry nitrogen atmosphere while being stirred at about −60° C. was treated dropwise with a solution of 1.45 g of DMSO (0.017 mole) in 5 ml of methylene chloride. Stirring at about −60° C. was continued 2 more minutes and a solution of 3.4 g (0.0077 mole) of the 8'-hydroxy compound, 1 (EP Appliclation No. 0,033,538), in 20 ml of methylene chloride was then added at a rate sufficient to maintain the temperature at −60° to −50° C. The mixture was stirred another 15 minutes and 6 ml of triethylamine was added and the mixture was allowed to warm to room temperature. The mixture was poured into 300 ml of ether, washed successively with 50 ml of water, 25 ml of brine, 10 ml of 1N hydrochloric acid and 25 ml of brine and dried over MgSO$_4$. Evaporation of the solvent under reduced pressure gave 3.4 g of an oil which solidified (m.p. 53°–56° C.) on standing overnight which was used without further purification in the next step.

Step B: Preparation of
6(R)-{2-[8'-hydroxyimino-2'(S),6'(S)-dimethyl-1',2',3',4',4'a(S),5',6',7',8',8'a(S)-decahydronaphthyl-1'(S)]-ethyl}-4(R)-(dimethyl-tert-butylsilyloxy)-3,4,5,6-tetrahydro-2H-pyran-2-one, (3)

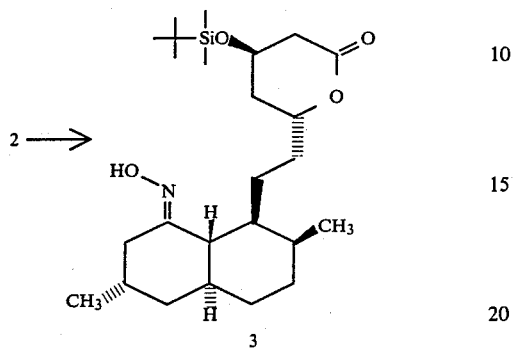

3

A mixture of 3.4 g (0.0077 mole) of the 8'-oxo compound, 2, from Step A, 2.5 g (0.0311 mole) of sodium acetate, 1.08 g (0.0155 mole) of hydroxylamine hydrochloride and 100 ml of 95% ethanol was stirred at room temperature overnight. The solvent was evaporated at 50° C. under vacuum. The residue was suspended in 250 ml ether and washed successively with 25 ml of water, 25 ml of brine, dried over MgSO4 and concentrated to dryness. The residue was purified by flash chromatography on silica gel (230–400 mesh) employing acetone/methylene chloride (5:95 v/v) as eluant. The appropriate fractions were combined and concentrated to dryness to give 2.5 g (72%) solid 8'-hydroximino compound, 3 m.p. 160°-162° C.

Step C: Preparation of
6(R)-{2-[8'(S)-amino-2'(S),6'(S)-dimethyl-1',2',3',4',4'a(S),5',6',7',8',8'a(S)-decahydronaphthyl-1'(S)]ethyl}-4(R)-dimethyl-tert-butylsilyloxy)-3,4,5,6-tetrahydro-2H-pyran-2-one, (4)

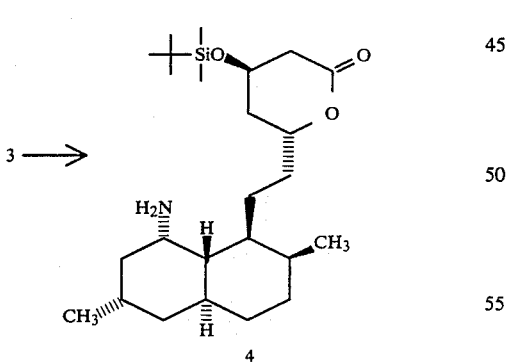

4

The 8'-hydroxyimino compound, 3, from Step B (0.5 g, 0.0011 mole) was dissolved in 25 ml of acetic acid. Platinum oxide (0.25 g) was added and the mixture was hydrogenated overnight. The catalyst was removed by filtration and the filtrate was concentrated in vacuo to an oil. The oil was dissolved in 200 ml of ether and washed successively with 2×20 ml of saturated sodium bicarbonate and 2×20 ml of brine, dried over MgSO4 and filtered. The filtrate was concentrated to 0.47 g of 4 (97%) of a colorless, viscous oil.

Step D: Preparation of
6(R)-{2-[8'(S)-(2",2"-dimethylbutyrylamino)-2'(S),6'(S)-dimethyl-1',2',3',4',4'a(S),5',6',7',8',8'a(S)-decahydronaphthyl-1'(S)]ethyl}-4(R)-(dimethyl-tert-butylsilyloxy)-3,4,5,6-tetrahydro-2H-pyran-2-one, (5)

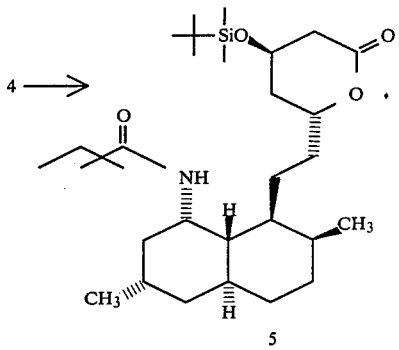

5

A solution of 0.55 g (0.00125 mole) of the 8'-amine, 4, from Step C in 10 ml of pyridine was cooled in an ice-bath and 0.338 g (0.0025 mole) of 2,2-dimethylbutyryl chloride was added dropwise with stirring. After 4 hours the reaction mixture was poured into 200 ml of ether and the solution was washed successively with 10 ml portions of 3N hydrochloric acid until the wash remained acidic to litmus paper, then with 10 ml of saturated sodium bicarbonate solution and 2×10 ml of brine and dried over MgSO4. Concentration to dryness gave an oil which was flash chromatographed on silica gel (230–400 mesh) with elution by acetone/methylene chloride (5:95 v/v). Combination and evaporation of the appropriate fractions gave 550 mg (82%) of the desired product, 5, as a foam.

Step E: Preparation of 6(R)-{2-['(S)-2",2"-dimethylbutrylamino)-2'(S),6'(S)-dimethyl-1',2',3',4',4'a(S),5',6',7',8',8'a(S)-decahydronaphthyl-1'(S)]ethyl}-4(R)-hydroxy-3,4,5,6-tetrahydro-2H-pyran-2-one, (6)

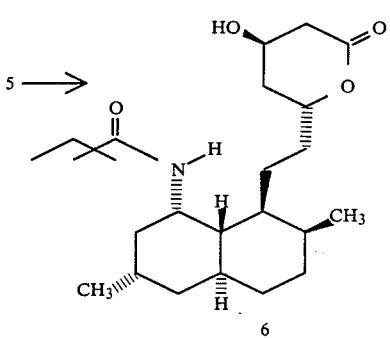

6

To a solution of 0.473 g (0.0015 mol) of Bu4N+F−.3H2O and 0.12 g (0.002 mol) of acetic acid in 10 ml of tetrahydrofuran was added 0.268 g (0.0005 mol) of the silyl ether, 5, from Step D. This mixture was stirred at 20° under a nitrogen atmosphere for 72 hours. The reaction mixture was diluted with 100 ml of ether and washed successively with 10 ml of 3N hydrochloric acid, 10 ml of saturated aqueous NaHCO3 and 2×10 ml of brine. The organic solution was dried (MgSO4) and filtered. Evaporation of the solvent left 234 mg of oil.

The oil was flash chromatographed on silica gel (230–400 mesh) by elution with acetone/methylene chloride (30:70 v/v). Collection, combination and evaporation of the appropriate fractions gave 169 mg of a solid which was recrystallized from about 5 ml ether and sufficient hexane to cause incipient cloudiness to give the pure compound, m.p. 92°–96° C. Calcd as ¼ hydrate: C, 70.46; H, 10.29; N, 3.29 Found: C, 70.56; H, 10.57; N, 3.20.

Employing the procedure substantially as described in Example I but substituting for the 2,2-dimethylbutyryl chloride used in Step D thereof, an equimolecular amount of the acid chlorides of structure

described in Table I, there are produced the 8-acylamino compounds also described in Table I in accordance with the following reaction scheme:

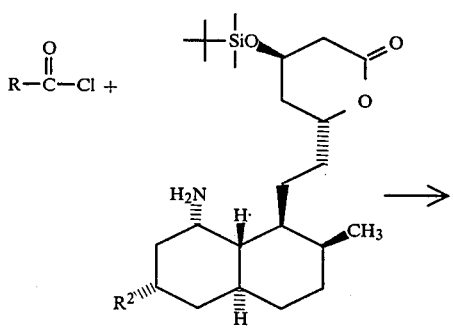

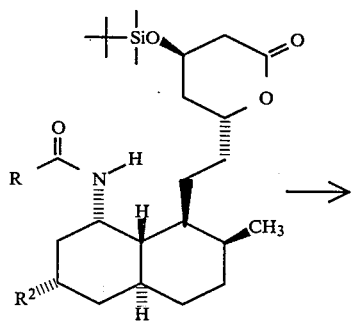

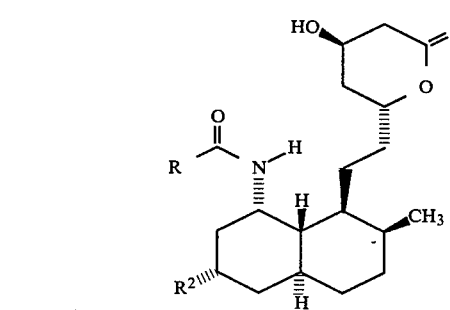

TABLE I

| R (R-CO-) | $R^2$ | m.p. (°C.) | Calcd | Found |
|---|---|---|---|---|
| (CH₃)₂C(CH₃)CH₂- (2,2-dimethylbutyryl) | CH₃ | glass | C: 71.68<br>H: 10.41<br>N: 3.22 | 71.93<br>10.81<br>2.90 |
| CH₃CH₂CH(CH₃)- | CH₃ | 90–93 | C: 69.94<br>H: 10.15<br>N: 3.40 | 69.70<br>10.11<br>3.14 |
| (CH₃)₃C- | H | | | |
| CH₃CH₂CH(CH₃)- | H | | | |
| (CH₃)₂CH- | CH₃ | | | |
| F₃C- | CH₃ | | | |
| (CH₃)₂CH- | CH₃ | | | |

EXAMPLE 2

6(R)-{2-[8'(S)-(4''-fluorobenzoylamino)-2'(S),6'(S)-dimethyl-1',2',3',4',4'a(S),5',6',7',8',8'a(S)-decahydronaphthyl-1'(S)]ethyl}-4(R)-hydroxy-3,4,5,6-tetrahydro-2H-pyran-2-one, (8)

Step A: Preparation of 6(R)-{2-[8'(S)-(4''-fluorobenzoylamino)-2'(S),6'(S)-dimethyl-1',2',3',4',4'a(S),5',6',7',8',8'a(S)-decahydronaphthyl-1'(S)]ethyl-}4(R)-(dimethyl-tert-butylsilyloxy)-3,4,5,6-tetrahydro-2H-pyran-2-one (7)

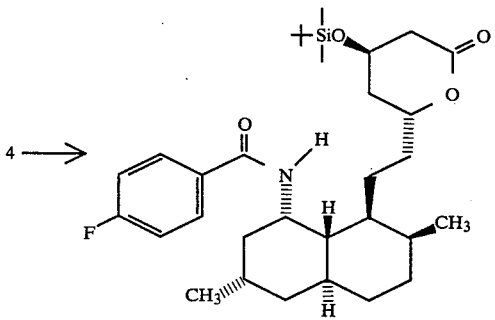

The 4(R)-(dimethyl-tert-butylsilyloxy)-8'(S)-amino compound, 4, (0.218 g, 0.5 mmol) from Example 1, Step C was added to a stirred mixture of 0.155 g (0.75 mmol) of dicyclohexylcarbodiimide, 0.105 g (0.75 mmol) of 4-fluorobenzoic acid and 10 ml of methylene dichloride. After stirring overnight at room temperature, the mixture was filtered and the filtrate was diluted with 100 ml of ether. The mixture was washed successively with 10 ml of saturated sodium bicarbonate solution, 10 ml of 3N hydrochloric acid and 2×20 ml of brine and dried over MgSO₄. Filtration and evaporation gave a semi-solid crude product which was flash chromatographed on silica gel (230–400 mesh) by elution with acetone/methylene chloride (2.5-97.5 v/v). Combination and evaporation of the appropriate fractions gave 0.25 g (89%) of the desired product, m.p. 194°–195° C.

Step B: Preparation of 6(R)-{2-[8'(S)-(4''-fluorobenzoylamino)-2'(S),6'(S)-dimethyl-1',2',3',4',4'a(S),5',6',7',8',8'a(S)-decahydronaphthyl-1'(S)]ethyl}-4(R)-hydroxy-3,4,5,6-tetrahydro-2H-pyran-2-one, (8)

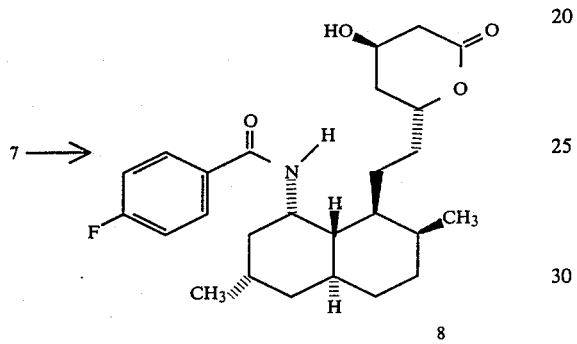

Employing the procedure of Example 1, Step E, but substituting for the 8'(S)-(2'',2''-dimethylbutyrylamino) compound used therein as starting material, an equimolecular amount of the 8'(S)-(4''-fluorobenzoylamino) compound from Example 2, Step A there was produced the desired product with m.p. 109°–113° C.

Calculated for hemihydrate; C, 68.69; H, 8.21, N. 3.08. Found: C, 68.38; H, 8.58; N, 2.95.

Employing the procedure substantially as described in Example 2 but substituting for the 4-fluorobenzoic acid used in Step A thereof, an equimolar amount of the acid of structure

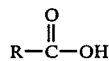

described in Table II, there are produced the 8-acylamino compounds also described in Table II in accordance with the following reaction scheme.

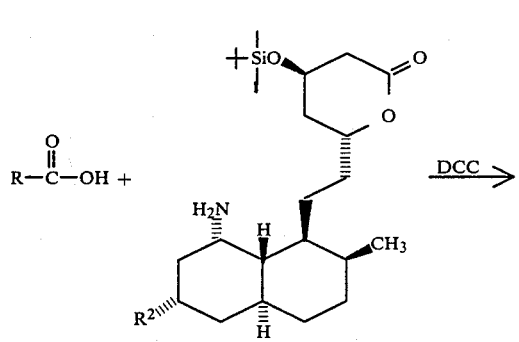

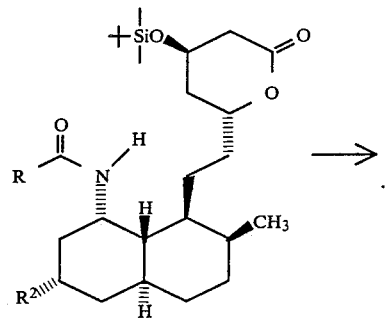

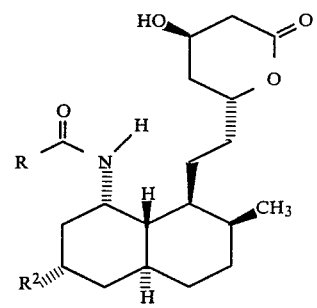

TABLE II

| R–C(O)– | R² | m.p. (°C.) | Calcd. | Found |
|---|---|---|---|---|
| F-C₆H₄-C(O)- | CH₃— | 101–106 | C: 68.85<br>H: 8.47<br>N: 2.77 | 69.09<br>8.67<br>2.66 |
| (CH₃)₃C-C₆H₄-C(O)- | CH₃ | 85 (eff.) | C: 73.13<br>H: 9.41<br>N: 2.84 | 73.16<br>9.77<br>2.91 |
| F,CH₃-C₆H₃-C(O)- | CH₃ | | | |
| F,CH₃-C₆H₃-C(O)- | H | | | |

EXAMPLE 3

6(R)-{2-[8'(S)-Acetylamino-2'(S),6'(R)-dimethyl-1',2',6',7',8',8'a(S)-hexahydronaphthyl-1'(S)]ethyl}-4(R)-hydroxy-3,4,5,6-tetrahydro-2H-pyran-2-one Step A: Preparation of 6(R)-2-[8'-oxo-2'(S),6'(R)-dimethylhexahydronaphthyl-1'(S)]ethyl-(4R)-(dimethyl-tert-butyl-silyloxy)-2-(2-tetrahyropyranyloxy)-3,4,5,6-tetrahydro-2H-pyran. (10)

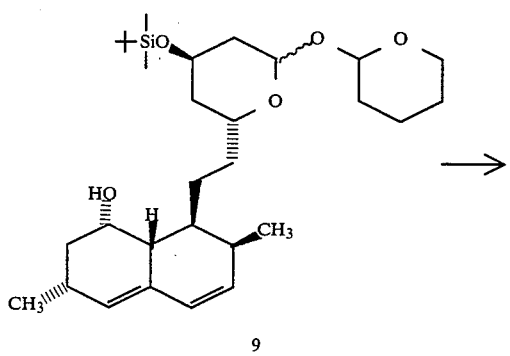

9

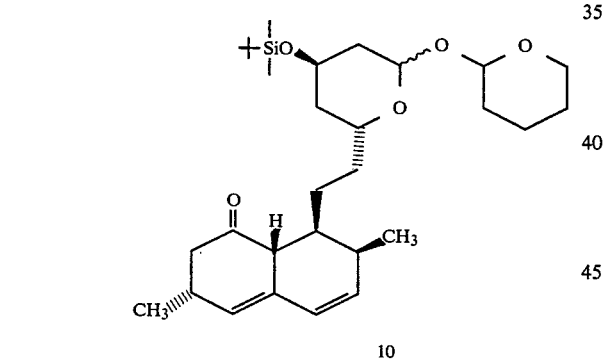

10

Employing the procedure of Example 1, Step A but using an equivalent quantity of 6(R)-2-[8'(S)-hydroxy-2'(S),6'(R)-dimethyl-1',2',6',7',8',8'a(S)-hexahydronaphthyl-1'(S)]ethyl-4(R)-(dimethyl-tert-butyl-silyloxy-2-(2-tetrahydropyranyloxy)-3,4,5,6-tetrahydro-2H-pyran, 9 (U.S. Pat. No. 4,282,155), as starting material, there was obtained the desired product 10 (41%) as a gummy oil: NMR (CDCl$_3$) δ 0.07 (6H, s), 0.09 (9H, s), 1.14 (3H, d, J=7 Hz), 3.3–4.0 (3H, m), 4.23 (1H, m), 4.9–5.3 (2H, m), 5.5 (1H, m), 5.80 (1H, dd, J=10, 6 Hz), 6.03 (1H, d, J=10 Hz), IR (neat) 1710 cm$^{-1}$.

Step B: Preparation of 6(R)-{2-[8'-Hydroxyimino-2'(S),6'(R)-dimethyl-1',2',6',7',8',8'a(S)-hexahydronaphthyl-1'(S)]ethyl}-4(R)-(dimethyl-tert-butylsilyloxy)-2-(2-tetrahydropyranyloxy)-3,4,5,6-tetrahydro-2H-pyran (11)

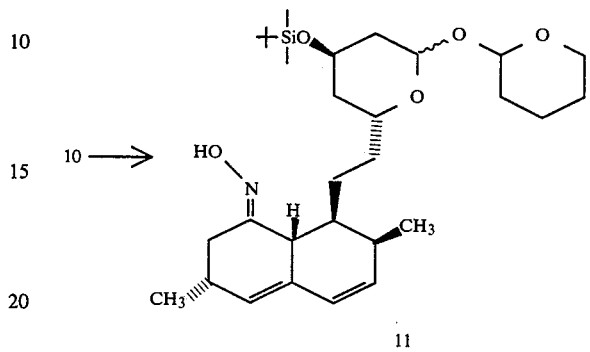

11

Employing the procedure of Example 1, Step B but using an equivalent quantity of the product 10 from Step A of this Example, there was produced the desired product 11, as a gummy oil (62%): NMR (CDCl$_3$)δ 0.04 (6H, s), 0.88 (9H, s), 1.11 (3H, d, J=7 Hz), 2.83 (1H, d, J=12 Hz), 3.00 (1H, dd, J=12, 4 Hz), 4.24 (1H, m), 5.40 (1H, m), 5.80 (1H, dd, J=10, 6 Hz), 6.01 (1H, d, J=10 Hz); IR (neat) 3360 (br) 1660 (w) cm$^{-1}$.

Step C: Preparation of 6(R)-{2-[8'-Amino-2'(S), 6'(R)-dimethyl-1',2',6',7',8',8'a(S)-hexahydronaphthyl-1(S)]ethyl}-4(R)-(dimethyl-tert-butylsilyloxy)-2-(2-tetrahydropyranyloxy)-3,4,5,6-tetrahydro-2H-pyran (12) and (13)

11 →

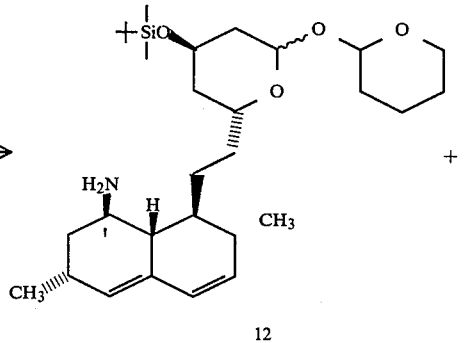

12

+

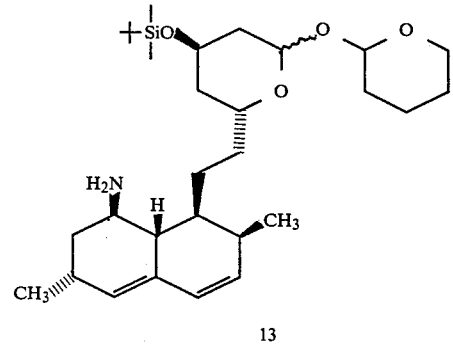

13

A solution of the 8′-hydroxyimino compound from Step B (200 mg, 0.375 mmol) in ether (3 ml) was added to a stirred suspension of powdered lithium aluminum hydride (70 mg, 1.84 mmol) in ether (7 ml) at 0° C. The resulting mixture was stirred at room temperature under nitrogen atmosphere for 16 hr. It was treated successively with water (70 μl), 20% sodium hydroxide (70 μl) and water (210 μl). The resulting mixture was stirred at room temperature for 0.5 hour, filtered and concentrated to yield an oily residue. This residue was purified by preparative TLC (eluant: methylene chloride/2-propanol=10/1 (v/v)) to give the starting material (60 mg, 30% recovery) and two amine products 12 [33 mg, 24% based on consumed starting material]; NMR (CDCl$_3$) δ 0.88 (9H, s), 1.20 (3H, d, J=7 Hz), 3.42 (1H, m), 3.53 (1H, m), 3.75–3.90 (2H, m), 4.27 (1H, m) 5.10 (1H, t), 5.15 (1H, dd, J=10, 2 Hz), 5.51 (1H, m), 5.80 (1H, dd, J=10, 6 Hz), 5.96 (1H, d, J=10 Hz); MS (m/e) 519 (M+) and 13 [34 mg, 24% based on consumed starting material]; NMR (CDCl$_3$) δ 0.88 (9H, s), 0.94 (3H, d, J=7 Hz), 1.04 (3H, d, J=7 Hz), 3.33 (1H, m), 3.51 (1H, m), 3.75–3.90 (2H, m), 4.26 (1H, m), 5.05 5.20 (2H, m), 5.47 (1H, m), 5.65 (1H, dd, J=10, 6 Hz), 5.96 (1H, d, J=10 Hz); MS (m/e) 519 (M+).

Step D: Preparation of 6(R)-{2-[8′(S)-Acetylamino-2′(S),6′(R)-dimethyl-1′,2′,6′,7′,8′,8′a(S)-hexahydronaphthyl-1′(S)]ethyl}-4(R)-(dimethyl-tert-butylsilyloxy)-2-(2-tetrahydropyranyloxy)-3,4,5,6-tetrahydro-2H-pyran. (14)

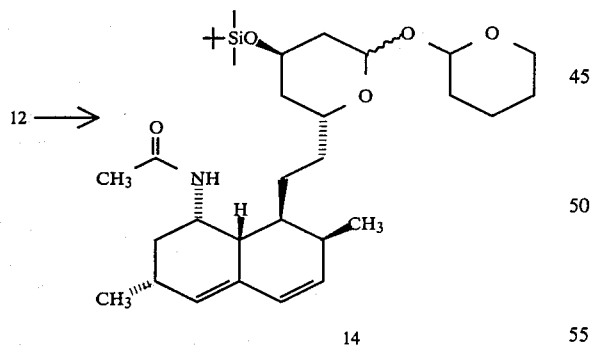

Employing the procedure of Example 1, Step D but using equivalent quantities of amine 12 and acetyl chloride in place of compound 4 and 2,2-dimethylbutyryl chloride respectively, there was obtained the desired product 14 as a gummy oil (79%): NMR (CDCl$_3$)δ 0.09 (9H, s), 1.08 (3H, d, J=7 Hz), 1.92 (3H, s), 3.55 (1H, m), 3.8 (2H, m), 4.25 (1H, m), 4.44 (1H, m), 5.07 (1H, t), 5.13 (1H, dd, J=10, 2 Hz), 5.35 (1H, d, J=9 Hz), 5.33 (1H, m), 5.85 (1H, dd, J=10, 6 Hz), 5.97 (1H, d, J=10 Hz).

Step E: Preparation of 6(R)-{2-[8′(S)-Acetylamino-2′(S),6′(R)-dimethyl-1′,2′,6′,7′,8′,8′a(S)-hexahydronaphthyl-1′(S)]ethyl}-4(R)-(dimethyl-tert-butylsilyloxy)-2-hydroxy-3,4,5,6-tetrahydro-2H-pyran. (15)

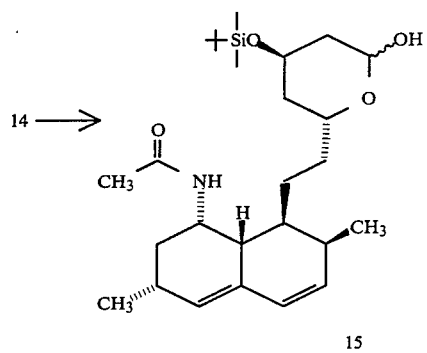

Powdered pyridinium p-tosylate (PPTS, 0.5 equiv) is added to a stirred solution of 14 in THF-HOAC-H$_2$O (3:1:1). The resulting mixture is stirred at room temperature for 48 hours, poured into cold water and extracted with ether. The ethereal extract is washed with water, aqueous sodium bicarbonate, dried over MgSO$_4$ and filtered. The filtrate is concentrated to yield a viscous residue which is purified by chromatography to give the desired product 15

Step F: Preparation of 6(R)-{2-[8′(S)-Acetylamino-2′(S),6′(R)-dimethyl-1′,2′,6′,7′,8′,8′a(S)-hexahydronaphthyl-1′(S)]ethyl}-4(R)-(dimethyl-tert-butylsilyloxy)-3,4,5,6-tetrahydro-2H-pyran-2-one (16)

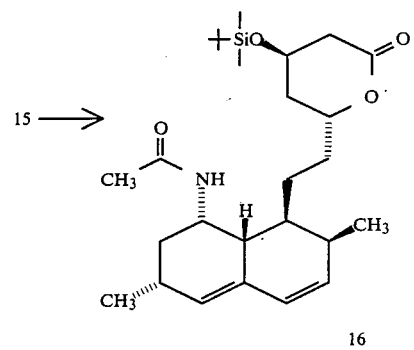

A mixture of 15 and freshly prepared silver carbonate-on-Celite in benzene is heated at reflux for 0.5 h under nitrogen atmosphere. The reaction mixture is cooled, filtered to remove the solid. The filtrate is concentrated to leave the desired 16 as a viscous oil.

Step G: Preparation of
6(R)-}2-[8'(S)-Acetylamino-2'(S),6'(R)-dimethyl-
1',2',6',7',8',8'a(S)-hexahydronaphthyl-1'(S)]ethyl}-4-
(R)-hydroxy-3,4,5,6-tetrahydro-2H-pyran-2-one. (17)

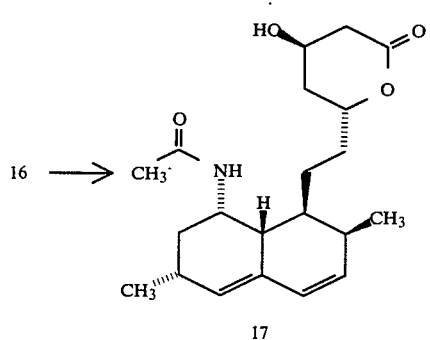

Employing the procedure of Example 1, Step E but using an equivalent quantity of silyl ether 16 in place of compound 5, there is produced the desired product 17.

EXAMPLE 4

6(R)-{2-[8'(R)-Acetylamino-2'(S),6'(R)-dimethyl-
1',2',6',7',8',8'a(S)-hexahydronaphthyl-1'(S)]ethyl}-
4(R)-hydroxy-3,4,5,6-tetrahydro-2H-pyran-2-one. (18)

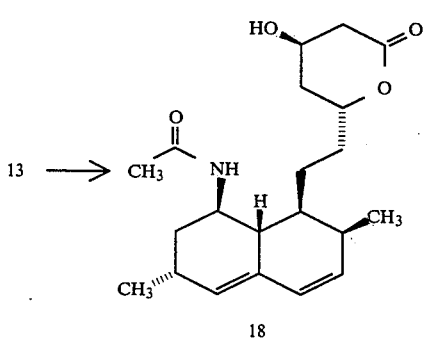

By following the same procedures described in Example 3, Steps D–G, but using an equivalent amount of amine 13 in place of 12, there is obtained the final end product 18.

Employing the procedure substantially as described in Examples 3 or 4, but substituting for the polyhydronaphthalene, 9, used in Step A and the acetyl chloride used in Step D thereof equimolecular amounts of the polyhydronaphthalenes and acid chlorides of structure

respectively identified in Table III, there are produced the end product polyhydronaphthalenes also identified in Table III:

TABLE III

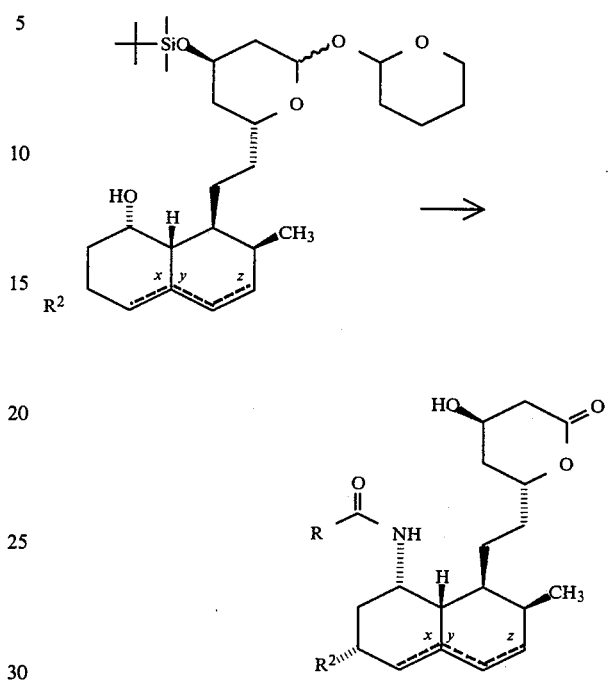

| R— | R² | X | Y | Z |
|---|---|---|---|---|
| 2,2-dimethylbutyryl | CH₃ | double | single | double |
|  | CH₃ | single | single | double |
|  | H | single | single | double |
|  | CH₃ | single | double | single |
|  | H | double | single | double |
| 2-methylbutyryl | CH₃ | double | single | single |
|  | CH₃ | double | single | double |
|  | CH₃ | single | single | double |
|  | H | single | single | double |
|  | CH₃ | single | double | single |
|  | H | double | single | double |
| 2-ethyl-2-methylbutyryl | CH₃ | double | single | double |
| cyclopropylcarbonyl | H | double | single | double |
| cyclohexylcarbonyl | CH₃ | single | single | double |
| 2,2,3-trimethyl-3-butenoyl | H | single | double | single |
| benzoyl | H | double | single | double |
| 3,4-dimethoxybenzoyl | H | single | single | double |
| phenylacetyl | CH₃ | single | double | single |
| 3,4-dimethoxyphenylacetyl | CH₃ | double | single | double |

EXAMPLE 5

6(R)-2-[8'(S)-(N-Methylacetylamino)-2'(S),6'(S)-dimethyl-1',2',3',4',4'a(S),5',6',7',8',8'a(S)-decahydronaphthyl-1'(S)]ethyl-4-(R)-hydroxy-3,4,5,6-tehahydro-2H-pyran-2-one, (21)

Step A: Preparation of
6(R)-2-[8'(S)-(N-methylamino)-2'(S),6'(S)-dimethyl-1',2',3',4',-4'a(S),5',6',7',8',8'a(S)-decahydronaphthyl-1'(S)]ethyl-4-(R)-(dimethyl-tert-butylsilyloxy)-3,4,5,6-tetrahydro-2H-pyran-2-one, (19)

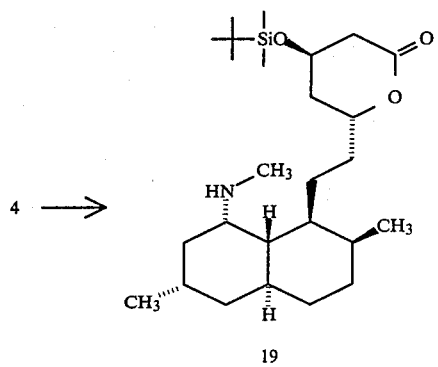

19

A solution of 104 mg (0.000237 mole) of the amine, 4 (Example 1, Step C) and 67.4 mg (0.000474 mole) of $CH_3I$ in DMF (5 ml) was stirred at ambient temperature for 48 hours. The reaction was diluted with ether (100 ml) and the resultant solution was washed with $H_2O$ (10 ml) and brine (2×10 ml) and dried over $MgSO_4$. Filtration and evaporation gave a viscous oil (88 mg). The oil was chromatographed on a 30 mm column containing 15.25 cm of silica gel (220–400 mesh). Elution with methanol-methylene chloride (1:19, V:V, 400 ml) gave a forerun which was discarded. Continued elution with the same eluant (150 ml) provided the title compound as a viscous oil (30 mg, 28%) NMR $(CDCl_3)$ δ 0.08 (6H, s), 0.83 (3H, d,J=7 Hz), 0.88 (9H, s), 1.19 (3H, d, J=7 Hz), 2.61 (5H, m) 3.10 (H, m), 4.28 (H, m), 4.70 (H, m).

Step B: Preparation of
6(R)-{2-[8'(S)-(N-Methylacetylamino)-2'(S),6'(S)-dimethyl-1',2',3',4',4'a(S),5',6',7',8',8'a(S)-decahydronaphthyl-1'(S)]ethyl}-4(R)-(dimethyl-tert-butylsilyloxy)-3,4,5,6-tetrahydro-2H-pyran-2-one, (20)

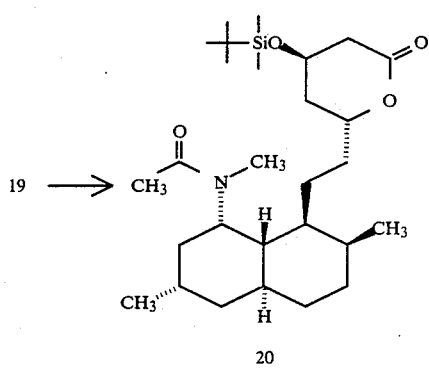

20

A solution containing 30 mg (0.0000664 mole) of the N-methylamino compound, 19, 20.3 mg (0.00019 mole) of acetic anhydride and 24.3 mg (0.00019 mole of 4-dimethylaminopyridine in methylene chloride (10 ml) was stirred at ambient temperature under a nitrogen atmosphere for 18 hours. The solution was diluted with ether (100 ml) and the resulting mixture was washed with 1N HCl (2×5 ml) and brine (2×10 ml) and dried over $MgSO_4$. Filtration and evaporation gave a viscous oil (23 mg). The oil was chromatographed on a 30 mm column containing 15.25 cm of silica gel (230–400 mesh). Elution with acetone-methylene chloride (1:9, v:v, 110 ml) gave a forerun which was discarded. Continued elution with the same eluant (90 ml) provided the title compound 20, as a viscous oil (17.5 mg, 53%) NMR $(CDCl_3)$δ 0.08 (6H, s), 0.82 (3H, d,J=7 Hz), 0.88 (12H, m), 2.19 (3H, s), 2.57 (2H, m), 3.0 (3H, s), 4.30 (H, m), 4.65 (H, m), 5.08 (H, m), MS (m/e) 493 (M+).

Step C: Preparation of
6(R)-{2-[8'(S)-(N-methylacetylamino)-2'(S),6'(S)-dimethyl-1',2',3',4',4'a(S),5',6',7',8'a(S)-decahydronaphthyl-1'(S)]ethyl}-4-(R)-hydroxy-3,4,5,6-tetrahydro-2H-pyran-2-one, (21)

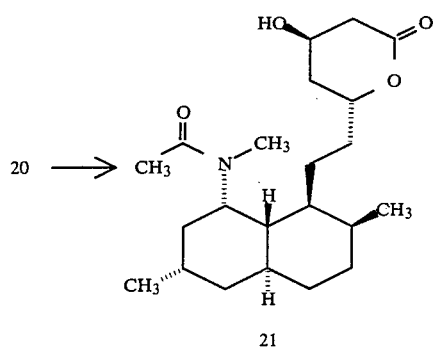

21

By following the procedure of Example I Step E, but substituting an equimolar amount of the silyl ether, 20, for the silylether, 5, there was obtained a corresponding amount of the title compound, 21.

Employing the procedure substantially as described in Example 4, but substituting for the methyl iodide used in Step A and the acetic anhydride used in Step B thereof equimolecular amounts of an alkylating agent of structure $R^1$-X, wherein X is Br or I and an acid anhydride of structure

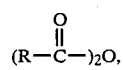

respectively described in Table IV there are produced the end products also described in Table IV in accordance with the following reaction scheme:

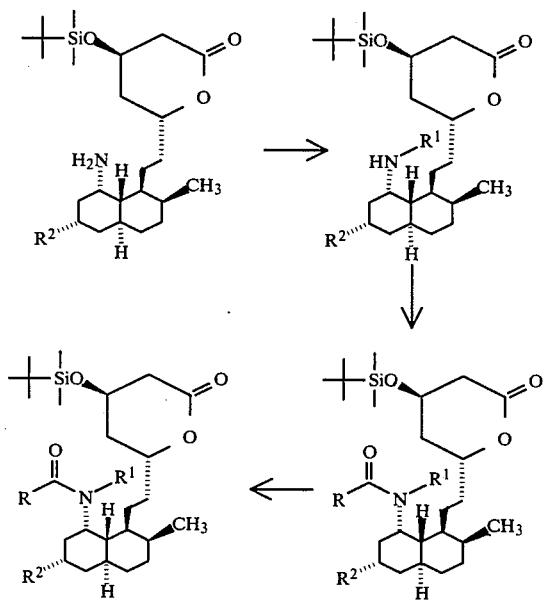

TABLE IV

| R | R¹ | R² |
|---|---|---|
| (isobutyryl, 2,2-dimethylpropanoyl group shown) | CH₃— | CH₃— m.p. 123-4° C. |
| | CH₃— | H |
| | n-C₃H₇— | CH₃— |
| | c-C₆H₁₁— | CH₃— |
| | CH₂=CH—CH₂— | CH₃— |
| | F₃CCH₂— | H |
| | C₆H₅CH₂— | CH₃— |
| | 4-F—C₆H₄CH₂CH₂ | CH₃— |

EXAMPLE 6

7-[1',2',3',4',4'a(S),5',6',7',8',8'a(S)-Decahydro-2'(S),6'(S)-dimethyl-8'(S)-[2",2"-dimethyl-butyrylamino]-1'(S)-naphthyl]-3(R),5(R)-dihydroxyheptanoic Acid To a stirred suspension of the lactone from Example 1, Step E, (40 mg, 0.095 mmol) in methanol (0.25 ml) is added sodium hydroxide (1N, 0.2 ml) and water (0.2 ml). The resulting mixture is stirred at room temperature until it becomes a clear solution. The solution is cooled in an ice bath and there are added successively CDCl₃ (1 ml), hydrochloric acid (2N, 0.15 ml) and water (0.5 ml). The resulting mixture is stirred for 15 minutes. The bottom organic layer is withdrawn by a transfer pipette.

The organic extract is dried (MgSO₄), and filtered through glass wool. The NMR and TLC analyses of the filtrate establishes the identity of the title compound.

EXAMPLE 7

7-[1',2',3',4',4'a(S),5',6',7',8',8'a(S)-Decahydro-2'(S),6'(S)-dimethyl-8'(S)-[2",2"-dimethyl-butyrylamino]-1'(S)-naphthyl]-3(R),5(R)-dihydroxyheptanoic Acid Ammonium Salt To a stirred suspension of the lactone from Example 1, Step E (0.3 g, 0.71 mmol) in methanol (2.1 ml) is added sodium hydroxide (1N, 1.47 ml) and water (2.1 ml). The resulting mixture is stirred at room temperature for 1 hour. Then, the methanol is evaporated in vacuo at 25° C. Ether (4 ml) is added to the residue. Subsequently, the mixture is acidified with hydrochloric (3N) under cooling with an ice-acetone bath. The aqueous layer is again extracted with ether (2×10 ml). The combined organic extracts are washed with saturated sodium chloride solution and dried (MgSO₄). After removal of the drying agent by filtration, the filtrate is treated with anhydrous ammonia gas for 2 minutes. After standing at room temperature for 1 hour, the title compound is collected.

EXAMPLE 8

Ethyl 7-[8'(S)-(2",2"-dimethylbutyrylamino)-2'(S),6'(S)-dimethyl-1',2',3',4',4'a(S),5',6',7',8',8'a(S)-decahydronaphthyl-1(S)]-3(R),5(R)-dihydroxyheptanoate Sodium methoxide (30 mg) is added to a stirred solution of the lactone from Example 1, Step E (3.0 g) in ethanol (50 ml) under a nitrogen atmosphere. The resultant solution is stirred at ambient temperature for ½ hour and then diluted with ether (300 ml). The ethereal solution is washed with H₂O (3×50 ml), dried over MgSO₄ and filtered. The filtrate is evaporated in vacuo leaving an oil which is chromatographed on a 60 mm column containing 15.25 cm silica gel (230–400 mesh). Elution with methylene chloride/ethanol (96:4, V:V) under air pressure gives the title compound.

EXAMPLE 9

2,3-Dihydroxypropyl 7-[8'(S)-(2",2"-dimethylbutyrylamino)-2'(S),6'(S)-dimethyl-1',2',3',4',4'a(S),5',6',7',8',8'a(S)-decahydronaphthyl-1(S)]-3(R),5(R)-dihydroxyheptanoate The sodium salt of the dihydroxy acid of the compound from Example 1, Step E is prepared by adding 1N NaOH (0.55 ml) to a solution of the lactone, 0.22 g in DMF (2 ml). After stirring this solution for 15 minutes, 1-iodo-2,3-dihydroxypropane (0.2 g) is added and the stirred solution is heated at 80° C. (oil bath) for 6 hours. After cooling to ambient temperature, the reaction solution is poured into ether (100 ml). This ethereal solution is washed with brine (2×25 ml), dried over MgSO₄ and filtered. The filtrate is evaporated in vacuo leaving an oil which is chromatographed on a 20 mm column containing 6" of silica gel (230–400 mesh). Elution with acetonemethylene chloride (60:40; v:v) under air pressure provides the title compound.

EXAMPLE 10

Typical formulations for filling a size 0 hard gelatin capsule comprising 3.125, 6.25, 12.5, 25 or 50 mg of one of the novel compounds of this invention such as the products of Examples 1–9 and sufficient finely divided lactose to provide a total capsule content of about 580–590 mg.

What is claimed is:
1. The compound of structural formula:

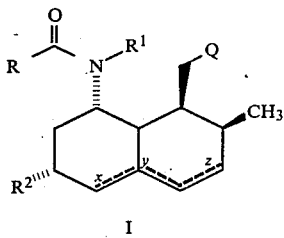

I wherein
Q is:

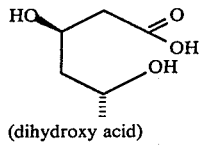

(dihydroxy acid)

or a pharmaceutically acceptable salt, $C_{1-3}$ alkyl ester or α-monoglyceride of the dihydroxy acid wherein $R^2$ is hydrogen or methyl;
R is
 (1) $C_{1-10}$ alkyl, either straight or branched chain,
 (2) $C_{3-6}$ cycloalkyl,
 (3) $C_{2-10}$ alkenyl,
 (4) halo-$C_{1-10}$ alkyl,
 (5) phenyl,
 (6) phenyl substituted by one or more of halo, $C_{1-3}$ alkyl, or $C_{1-3}$ alkoxy,
 (7) phenyl-$C_{1-3}$ alkyl,
 (8) phenyl-$C_{1-3}$ alkyl wherein the phenyl group is substituted by one or more of halo, $C_{1-3}$ alkyl, or $C_{1-3}$ alkoxy;
$R^1$ is
 (1) hydrogen,
 (2) $C_{1-3}$ alkyl,
 (3) $C_{3-6}$ cycloalkyl,
 (4) $C_{2-5}$ alkenyl,
 (5) halo-$C_{1-3}$ alkyl,
 (6) benzyl, or
 (7) benzyl, substituted by one or more of halo, $C_{1-3}$ alkyl, or $C_{1-3}$ alkoxy; and
the dotted lines X, Y and Z, represent possible double bonds, the double bonds, when any are present being either X and Z in combination or one of X, Y or Z alone.

2. The compound of claim 1 wherein R is 1-methylpropyl, 1,1-dimethylpropyl or 1-ethyl-1-methyl-propyl; $R^1$ is hydrogen or methyl; X and Z are double bonds; or X, Y and Z are all single bonds; or a pharmaceutically acceptable salt, $C_{1-3}$ alkyl ester or α monoglyceride of structure of the dihydroxy acid.

3. The compound of claim 2, which is

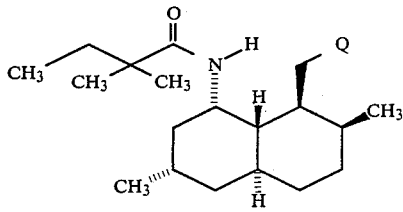

or a pharmaceutically acceptable salt, $C_{1-3}$ alkyl ester, or α-monoglyceride of the dihydroxy acid.

4. An antihypercholesterolemic pharmaceutical composition comprising a pharmaceutical carrier and an effective antihypercholesterolemic amount of the compound of claim 1, or a pharmaceutically acceptable salt, $C_{1-3}$ alkyl ester or α-monoglyceride of the dihydroxy acid.

5. The composition of claim 4 wherein the compound is that of claim 3, or a pharmaceutically acceptable salt, $C_{1-3}$ alkyl or α-monoglyceride of the dihydroxy acid.

6. The composition of claim 5 wherein the compound is that of claim 4, or a pharmaceutically acceptable salt, $C_{1-3}$ alkyl or α-monoglyceride of the dihydroxy acid.

7. A method of treating atherosclerosis, familial hypercholesterolemia or hyperlipemia comprising administering to a patient in need of such treatment an effective antihypercholesterolemic amount of the compound of claim 1, or a pharmaceutically acceptable salt, $C_{1-3}$ alkyl or α-monoglyceride of the dihydroxy acid.

8. The method of claim 7 wherein the compound is that of claim 3, or a pharmaceutically acceptable salt, $C_{1-3}$ alkyl or α-monoglyceride of the dihydroxy acid.

9. The method of claim 8 wherein the compound is that of claim 4, or a pharmaceutically acceptable salt, $C_{1-3}$ alkyl or α-monoglyceride of the dihydroxy acid.

* * * * *